(12) United States Patent
Predina et al.

(10) Patent No.: US 7,095,007 B2
(45) Date of Patent: Aug. 22, 2006

(54) METHOD AND APPARATUS FOR MEASUREMENT OF OPTICAL DETECTOR LINEARITY

(75) Inventors: Joe Paul Predina, Fort Wayne, IN (US); Frederick Lee Williams, Fort Wayne, IN (US)

(73) Assignee: ITT Manufacturing Enterprises, Inc., Wilmington, DE (US)

(*) Notice: Subject to any disclaimer, the term of this patent is extended or adjusted under 35 U.S.C. 154(b) by 206 days.

(21) Appl. No.: 10/944,807

(22) Filed: Sep. 21, 2004

(65) Prior Publication Data

US 2006/0060759 A1    Mar. 23, 2006

(51) Int. Cl.
   *H01L 31/00*   (2006.01)
(52) U.S. Cl. .................. 250/214.1; 250/226
(58) Field of Classification Search ......... 250/214.1, 250/226, 216
   See application file for complete search history.

(56) References Cited

U.S. PATENT DOCUMENTS

| | | | |
|---|---|---|---|
| 2,143,094 A | 1/1939 | Swift | |
| 3,238,449 A | 3/1966 | Gordon et al. | |
| 4,258,314 A * | 3/1981 | Hirata | ............ 324/620 |
| 4,927,269 A | 5/1990 | Keens et al. | |
| 4,975,635 A | 12/1990 | Takahashi et al. | |
| 5,148,233 A | 9/1992 | Imamura et al. | |
| 5,229,833 A | 7/1993 | Stewart | |
| 5,831,731 A | 11/1998 | Hall et al. | |
| 6,252,668 B1 | 6/2001 | Hill | |
| 6,342,947 B1 | 1/2002 | Gillino | |
| 6,608,293 B1 | 8/2003 | Kuderer | |

2003/0030816 A1    2/2003 Eom et al.

FOREIGN PATENT DOCUMENTS

| JP | 54-73690 A | 6/1979 |
|---|---|---|
| JP | 1055836 A | 3/1989 |
| JP | 9-264780 A | 10/1997 |

OTHER PUBLICATIONS

Kubarsepp et al. "Nonlineraity Measurements of Silicon Photodetectors", Applied Optics, vol. 37, No. 13, May 1, 1998, pp. 2716-2722.
Shao et al. "Optical Detector Nonlinearity: a Comparison of Five Methods" Proceedings of Conference on Precision, Electromagnetic Measurements Digest, Jul. 1, 1994, pp. 455-456.

* cited by examiner

*Primary Examiner*—Que T. Le
(74) *Attorney, Agent, or Firm*—Edell, Shapiro & Finnan, LLC

(57) ABSTRACT

A system for measuring optical detector linearity according to the present invention employs a laser source that illuminates an integrating sphere. The sphere randomizes the laser signal phase and produces a uniform intensity over the sphere output. A collimator expands the sphere output for entry into an interferometer, where the incident optical energy is amplitude modulated in a sinusoidal fashion by a linear mechanical mirror movement. Optical band filters eliminate significant harmonic content being present on a pre-detected optical signal. Sampling of the detected signal energy is performed synchronous to the mechanical mirror position to assure sinusoidal response. The sampled signals are processed to separately determine signal harmonic components attributed to detector non-linearity and multiple laser reflections within the system. The system utilizes at least two measurements at two different laser intensities. An optional third measurement of background radiance may be applied to the first two measurements to enhance accuracy.

38 Claims, 5 Drawing Sheets

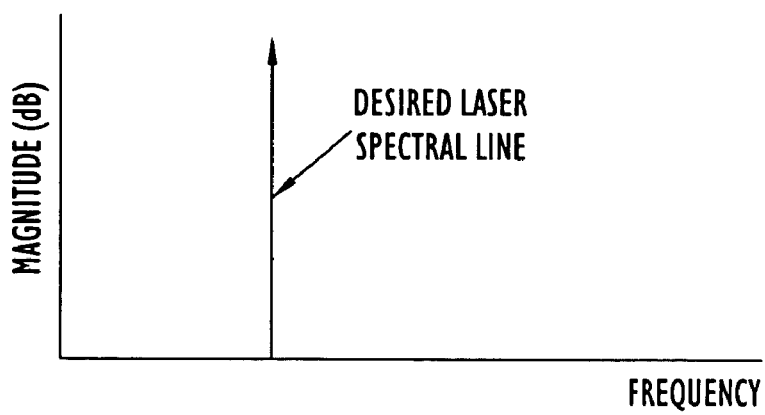
FIG. 3A Ⓐ
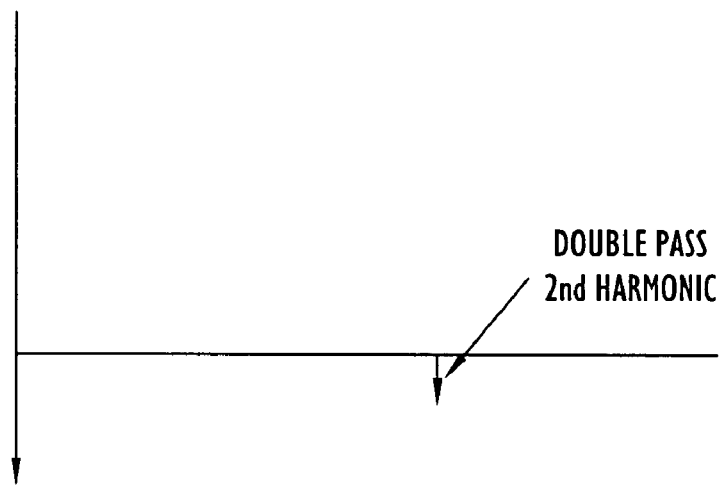
FIG. 3B Ⓑ+Ⓒ
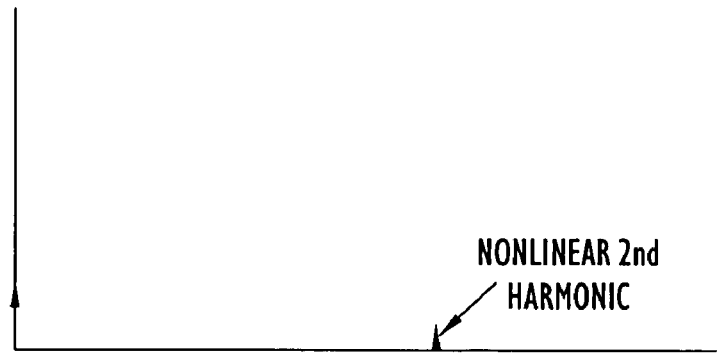
FIG. 3C Kd Ⓐ * Ⓐ

METHOD AND APPARATUS FOR MEASUREMENT OF OPTICAL DETECTOR LINEARITY

STATEMENT REGARDING FEDERALLY SPONSORED RESEARCH OR DEVELOPMENT

The U.S. Government may have a paid-up license in this invention and the right in limited circumstances to require the patent owner to license others on reasonable terms.

BACKGROUND OF THE INVENTION

1. Technical Field

The present invention pertains to systems for measuring properties of optical detectors. In particular, the present invention pertains to a system for measuring optical detector linearity by identifying signal portions attributed to detector non-linearity based on a harmonic analysis of measurement signals detected by the detector.

2. Discussion of the Related Art

Various instruments and devices employ optical detectors for operation. The characteristics of the detectors and associated electronics may adversely affect or distort results produced by the instruments or devices. Accordingly, the related art provides several techniques to measure detector characteristics, such as non-linearity. For example, a calibrated radiance target technique utilizes a black body radiator target and a change of target temperature. The photon flux emitted by the black body target is a function of temperature and allows a calculation of the photon energy striking an optical detector. Thus, changing the black body target temperature and measuring the detector response over the optical range of interest results in data that can be plotted and analyzed to determine non-linearity of response.

However, the calibrated radiance target technique suffers from several disadvantages. In particular, this technique is subject to substantial measurement errors due to black body targets reflecting optical radiance originating from the surrounding environment and the uncertainty in the black body target surface temperature. Further, the calibrated radiance target technique typically cannot be relied upon to perform non-linearity characterization to an accuracy better than 0.5% and requires expensive deep well cavity targets with precise temperature monitoring and a test set-up designed to limit environmentally induced errors. Moreover, this measurement technique cannot be performed fast enough to eliminate detector drift errors, while the target temperature is altered. In addition, the calibrated radiance target technique can only characterize linearity in a static DC sense and does not provide linearity characterization as a function of detector operating frequency.

A second method of performing non-linearity characterization involves a dual source progressive profiling technique. This technique uses two radiant sources illuminating an integrating sphere to measure non-linearity of an optical detector. One source or bulb is enabled and a measurement performed. The first bulb is disabled and the second source or bulb is enabled with bias adjusted on the second bulb to attain the same sensor or detector reading as the first bulb. Subsequently, both bulbs are enabled and the detector output should exactly double. This process of switching, comparing and doubling continues in a binary growth fashion until the entire range of interest is covered.

The dual source progressive technique suffers from several disadvantages. In particular, this technique incurs measurement errors due to the sources heating the integrating sphere and altering sphere characteristics. Thus, the dual source progressive technique requires the integrating sphere temperature to be well stabilized. Further, the technique is not fast enough to eliminate detector drift errors in response to the source targets changing temperature and does not perform well at IR wavelengths due to the uncertainty of the integrating sphere background radiance. Moreover, this technique can only characterize non-linearity in a static DC sense and does not provide characterization as a function of detector operating frequency.

A third method representative of the related art uses a harmonic analysis technique combined with an electrically modulated light emitting diode (LED) for measuring non-linearity of an optical detector. The bias current to an LED optical source is modulated in a sinusoidal fashion. The detected optical signal is processed through a spectrum analyzer to detect harmonics generated by the optical detector. The magnitude of each detector generated harmonic allows an assessment of non-linearity.

The LED harmonic analysis technique suffers from several disadvantages. In particular, this technique has limited performance capability due to non-linearity of the modulated optical source which is often greater than the detector undergoing characterization. Further, the LED harmonic analysis technique has a poor signal-to-noise (S/N) ratio to resolve harmonics due to the broadband emission of LED emitters.

A fourth method similar to the modulated LED technique uses harmonic analysis combined with an electrically modulated laser optical source for measuring non-linearity. A laser diode with sinusoidally modulated bias current serves as the optical source. The detected optical signal is processed through a spectrum analyzer to detect harmonics generated by the optical detector. The magnitude of each detector generated harmonic allows an assessment of non-linearity.

The laser harmonic analysis technique suffers from several disadvantages. In particular, this technique has limited performance capability due to non-linearity of the electrically modulated optical source which is often greater than the detector undergoing characterization. Further, the laser diode can only be successfully modulated over a small fraction of its output range, thereby introducing an unwanted optical bias for detector non-linearity characterization and a much reduced signal-to-noise ratio for making the characterization.

The present invention provides several advantages. The present invention employs harmonic analysis of a detected and sampled optical signal in combination with an opto-mechanical modulator of laser energy. The opto-mechanical modulator of laser energy combines with an optical filter to produce a harmonic-free sinusoidally modulated laser source for testing a detector. The opto-mechanical modulator further uses a metrology laser to measure movement of the opto-mechanical mechanism that produces the modulation. The detected optical signal is sampled synchronous to the modulator metrology laser, thereby assuring perfect sinusoidal modulation sampling regardless of the exact speed of the mechanical mirror movement of the modulator. The precision of the sinusoidally modulated optical source significantly exceeds that of the harmonic analyses described above, thereby enabling non-linearity measurements with enhanced accuracies (e.g., 0.01% or better).

The complete non-linearity measurement can be conducted by the present invention in a short time interval (e.g., a small fraction of one second), thereby eliminating measurement drift errors associated with the calibrated radiance target and dual source progressive techniques described above. Since the optical source is modulated at a specific sinusoidal frequency, all errors due to background radiance variation in the calibrated radiance target and dual source progressive techniques described above are also eliminated. The opto-mechanical modulator can be used to change modulation frequency allowing characterization over the detector frequency range which cannot be accomplished by calibrated radiance target and dual source progressive techniques described above.

The present invention employs a monochromatic laser diode rather than a broadband optical source as described above for the LED harmonic analysis technique. This allows a higher S/N ratio in the harmonic analysis and a characterization over a dynamic range one-hundred times greater than the calibrated radiance target, dual source progressive and LED harmonic analysis techniques described above. The use of a monochromatic laser diode further enables the spectrum analysis to differentiate between unmodulated photon flux and several sources of unmodulated background photon flux that lead to errors in the calibrated radiance target, dual source progressive and LED harmonic analysis techniques described above.

The present invention employs an opto-mechanical modulator with sampling synchronous to the modulator mirror movement, thereby providing enhanced performance and modulation over a wider portion of the source range relative to the laser harmonic analysis technique described above. Further, the present invention can produce a wider combination of modulated and unmodulated photon flux test combinations for testing dynamic non-linearity under various static optical flux biases which are not attainable by the calibrated radiance target and dual source progressive techniques described above.

The present invention may be applied to perform precision non-linearity characterization on scientific remote sensing instruments for climate and weather monitoring. However, the present invention may be applied on a broad scope, especially to those applications pertaining to establishing scientific standards for detector linearity and optical test equipment for UV, visible and IR detector characterization. The present invention can improve the accuracy of scientific instruments that must accurately measure incident photon flux.

OBJECTS AND SUMMARY OF THE INVENTION

Accordingly, it is an object of the present invention to measure non-linearity of optical detectors with enhanced accuracy.

It is another object of the present invention to measure non-linearity of optical detectors based on harmonic analysis.

Yet another object of the present invention is to employ an optical source modulated to include a sinusoidal flux to measure optical detector non-linearity.

Still another object of the present invention is to modulate an optical source signal for measuring detector non-linearity via the position of a movable mirror modulating that signal and to sample the detector based on the mirror position to ensure sinusoidal modulation of the signal and enhanced measurement accuracy.

A further object of the present invention is to measure detector linearity by identifying signal portions attributed to detector non-linearity within harmonics of a detected and sampled measurement signal.

Yet another object of the present invention is to separate signal portions within measured harmonics into a component associated with detector/electronic non-linearity and a second overlapping component associated with multiple optical reflections of an opto-mechanical modulator (e.g., unassociated with the detector/electronic non-linearity).

Still another object of the present invention is to enable adjustment of optical source intensity for enabling separation of the detector/electronic non-linearity component and the multiple optical reflection component.

The aforesaid objects may be achieved individually and/or in combination, and it is not intended that the present invention be construed as requiring two or more of the objects to be combined unless expressly required by the claims attached hereto.

According to the present invention, an optical system for measuring detector non-linearity employs a monochromatic laser source that illuminates an integrating sphere with a laser signal. The integrating sphere randomizes the phase of the coherent laser signal and produces a uniform optical intensity over the sphere output aperture. The sphere output is expanded to a larger aperture via a collimator. The monochromatic incoherent optical laser signal enters an opto-mechanical modulator or interferometer, where the incident optical energy is amplitude modulated in a sinusoidal fashion by a linear mechanical mirror movement. The interferometer produces a sinusoidally changing optical flux that passes through optical band pass filters. The filters eliminate any possibility of significant harmonic content being present on the pre-detected optical signal.

Sampling of the detected signal energy is performed synchronous to the mechanical mirror position to assure sinusoidal response regardless of the actual mechanical mirror movement rate. This near perfect sinusoid is recovered during post processing by triggering the sampling of detector response using a laser metrology unit that controls and measures mirror movement.

The sampled electrical signals are processed to determine signal components attributed to detector/electronic non-linearity and laser signal reflection. The system utilizes at least two measurements to perform the processing. A first measurement is performed with the laser source at maximum intensity, while a second measurement is performed with the laser source at reduced intensity. An optional third measurement of a cold black body target (e.g., background radiance) may be applied to the first two measurements to enhance measurement accuracy. The sampled signals produce data that enable the signal component attributed to detector non-linearity to be identified, thereby providing a non-linearity measurement for the detector.

The above and still further objects, features and advantages of the present invention will become apparent upon consideration of the following detailed description of specific embodiments thereof, particularly when taken in conjunction with the accompanying drawings wherein like reference numerals in the various figures are utilized to designate like components.

BRIEF DESCRIPTION OF THE DRAWINGS

FIGS. 3A–3C are graphical illustrations of the signal components of the measurement signal sampled from the optical detector.

DETAILED DESCRIPTION OF THE PREFERRED EMBODIMENTS

The present invention system generates optical signals for detection by a detector to determine the detector non-linearity. The generated signals are modulated and sampled in accordance with the position of a moving interferometer porchswing mirror to ensure sinusoidal modulation as described below. The sampled signal includes components respectively attributed to reflection of the signal within the optical system and/or detector non-linearity. These components are identified within the sampled signal based on a harmonic analysis, where the non-linearity component indicates the detector non-linearity as described below. The system optical arrangement and harmonic analysis enable the non-linearity measurement to be performed with enhanced accuracy.

Figure 1:
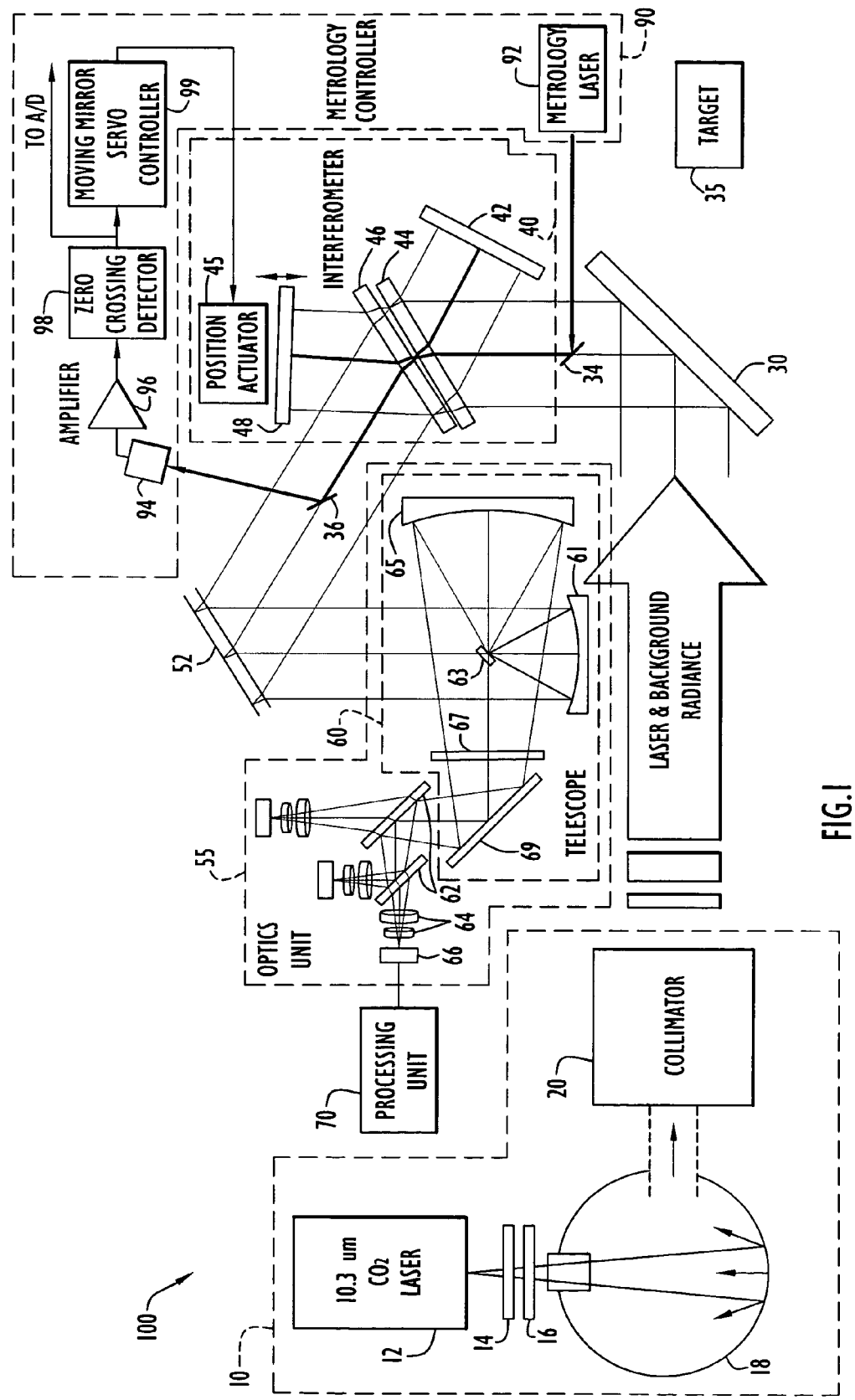
FIG. 1 is a diagrammatic illustration of a system for measuring optical detector linearity according to the present invention.
Figure 2:
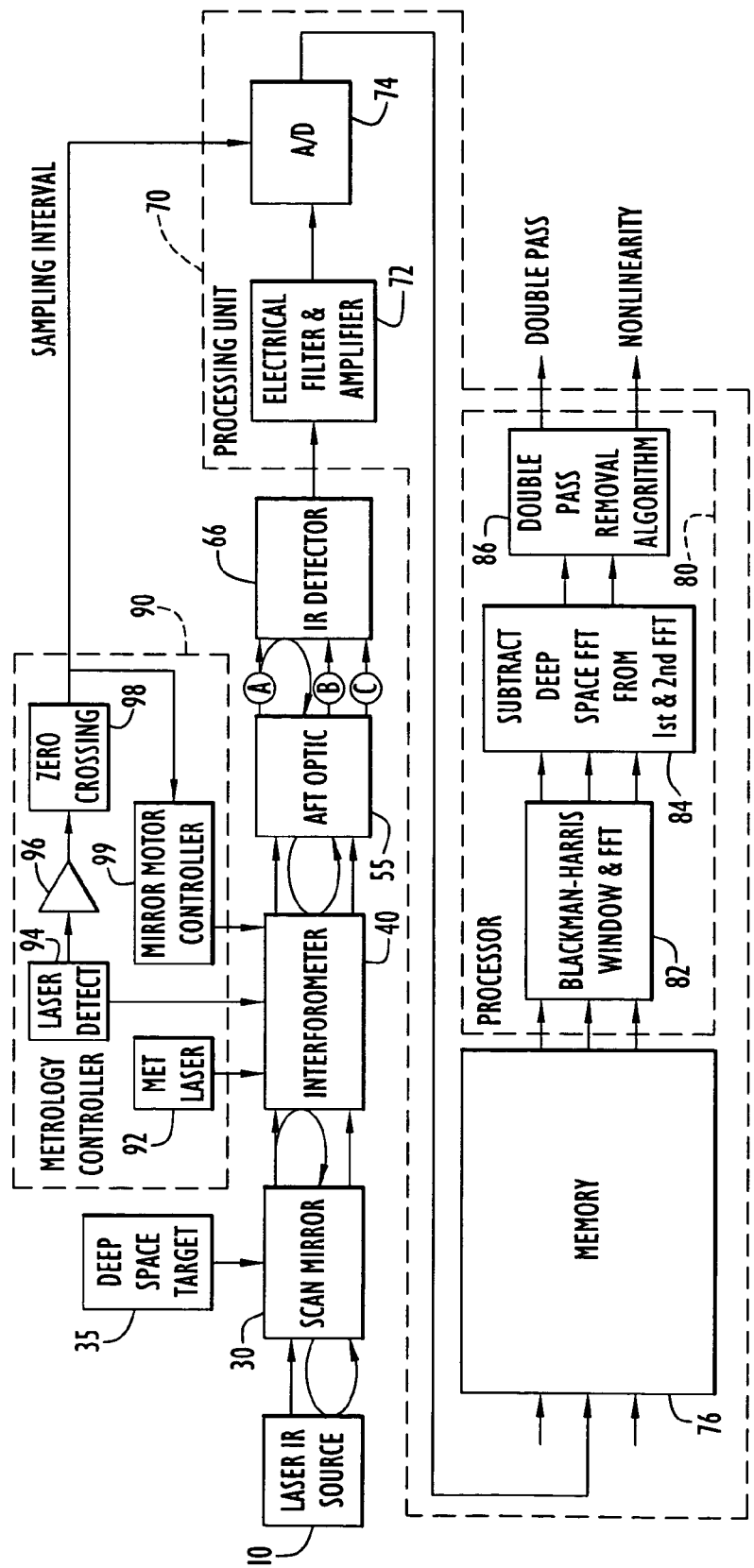
FIG. 2 is a block diagram of the system of FIG. 1 illustrating reflected signal paths through the system.

A system 100 for measuring detector non-linearity according to the present invention is illustrated in FIGS. 1–2. Specifically, system 100 includes a laser source 10, a scene select module 30, an interferometer 40, an optics unit 55, one or more detectors 66 and a processing unit 70. Laser source 10 includes a laser unit 12, an optical attenuator 14, a shutter attenuator 16, an integrating sphere 18 and a collimator 20. Laser unit 12 is preferably implemented by a 10.3 um $CO_2$ laser producing an infrared signal. However, the laser unit may be implemented by any type of laser or other light source producing narrow band radiation of any suitable wavelength within the capability of the detector. For example, a target having a very high temperature sufficient for the target to emit infrared radiation may be utilized, where a narrow band optical filter is disposed between that target and integrating sphere to produce the desired narrow band optical signal.

Laser unit 12 projects a source or measurement laser signal through optical and shutter attenuators 14, 16 to illuminate integrating sphere 18. The attenuators are positioned in a substantially transverse orientation within the system signal path and are disposed proximate each other in a substantially parallel relation with optical attenuator 14 disposed toward laser unit 12 and shutter attenuator 16 disposed toward integrating sphere 18. Optical attenuator 14 may be implemented by any conventional devices (e.g., lens, filter, etc.) and basically serves to limit the photon flux level of the laser signal to a desired range for the non-linearity measurement. The optical attenuator may be utilized to provide any desired photon flux level for the laser signal. The system may include a bank of attenuators with each attenuator selectively manipulable to be positioned within the system laser signal path.

Shutter attenuator 16 may be implemented by any conventional optical attenuator (e.g., lens, filter, shutter, LCD shutter, etc.) and serves to attenuate the energy of the source laser signal (e.g., by 30%, 50%, etc.) produced by the laser unit. The shutter attenuator is selectively manipulable to be positioned within the system laser signal path, where the attenuator is placed within the path for reduced intensity and removed from the path for maximum intensity. The present invention utilizes measurements with the laser signal at maximum and reduced intensities to measure detector non-linearity as described below.

Integrating sphere 18 receives the laser signal from the attenuators and randomizes the phase of the coherent laser signal to produce a uniform optical intensity over the sphere output aperture. The combination of the laser source, attenuators and integrating sphere enables adjustment of the laser intensity for the non-linearity measurement without changing the reflection coefficient of the integrating sphere. This enables adjustment of the laser intensity without affecting the fraction of the laser energy undergoing multiple reflection (e.g., from interferometer 40, back through collimator 20 to integrating sphere 18 and then back into collimator 20 and eventually into the interferometer). Further, the integrating sphere reduces the visibility of shutter attenuator 16 to collimator 20 and interferometer 40, where the collimator basically sees mostly the surfaces of the integrating sphere and a small part of the shutter attenuator.

The laser signal from the integrating sphere output enters collimator 20. The collimator expands the received signal to a full aperture (e.g., approximately eight centimeters) of interferometer 40. Alternatively, the system may employ a larger integrating sphere and a more powerful laser and be utilized without collimator 20. The sphere and collimator may be implemented by any conventional or other optical components performing the functions described herein.

The resulting monochromatic incoherent laser signal from collimator 20 is directed toward scene select module or scan mirror 30. The scene select module is preferably implemented by a pointing mirror that rotates between two positions. A first position directs the laser signal from collimator 20 to interferometer 40, while a second position directs optical energy from a cold black body target 35 to interferometer 40. Basically, the scene select module functions as a switch to direct the appropriate optical signal (e.g., laser signal from laser unit 12 or optical energy from the cold target) to the interferometer during the non-linearity measurement. The cold target optical signal essentially provides an indication of background radiance for the interferometer and may be utilized by the system to enhance accuracy of the detector non-linearity measurement as described below. Alternatively, the scene select module may be implemented by or include any conventional or other optical devices (e.g., lens, mirror, telescope, etc.).

The laser signal from scene select module 30 enters interferometer or opto-mechanical modulator 40 that produces a sinusoidally modulated optical signal. In particular, the interferometer includes a dynamic alignment module 42, beam splitters 44, 46 and a moving porchswing mirror 48. These components may be implemented by any conventional or other optical devices (e.g., mirrors, lenses, etc.). Porchswing mirror 48 is manipulable to perform a linear or distance movement toward or away from beam splitters 44, 46 to produce an amplitude modulated laser signal with a sinusoidally varying intensity as described below. The laser signal from scene select module 30 initially impacts beam splitters 44, 46. The beam splitters are disposed in a tilted fashion within the signal path between the scene select module and porchswing mirror. The beam splitters may be implemented by any conventional or other optical devices (e.g., lenses, splitters, etc.) and are disposed proximate each other in a substantially non-parallel fashion with beam splitter 44 disposed toward scene select module 30 and beam splitter 46 disposed toward porchswing mirror 48. Once the laser signal impacts beam splitter 44, approximately one-half of the laser signal energy is reflected from beam splitter 44 to dynamic alignment module 42, preferably implemented by a conventional or other mirror. The dynamic alignment module is disposed between the scene select module and beam splitter 44 but external of the signal path between those elements. The remaining portion of the laser signal traverses beam splitters 44, 46 to impact porchswing mirror 48.

The laser signal from beam splitter 44 is reflected by dynamic alignment module 42 back towards beam splitter 44 and includes approximately one-half of the total laser signal energy. The reflected laser signal from the dynamic alignment module impacts beam splitter 44, where approximately one-half of the reflected laser signal energy is reflected from beam splitter 44 and impacts scene select module 30 to be directed toward collimator 20. The remaining portion of the laser signal impacting beam splitter 44 (e.g., including approximately one-quarter of the total energy of the laser signal initially entering the interferometer) traverses beam splitters 44, 46 and is directed from interferometer 40 to a fold mirror 52. The fold mirror directs the laser beam to optics unit 55.

The laser signal from beam splitters 44, 46 impacting porchswing mirror 48 is reflected from the porchswing mirror and includes approximately one-half of the total laser signal energy. The reflected laser signal from the porchswing mirror impacts beam splitter 46, where approximately one-half of the reflected laser signal energy (e.g., including approximately one-quarter of the total energy of the laser signal initially entering the interferometer) traverses beam splitters 46, 44 to impact scene select module 30 to be directed toward collimator 20. The remaining portion of the laser signal impacting beam splitter 46 (e.g., including approximately one-quarter of the total energy of the laser signal initially entering the interferometer) is reflected from interferometer 40 toward fold mirror 52. The fold mirror directs the laser signal to optics unit 55 as described above. Thus, approximately one-half of the energy of the laser signal entering the interferometer is reflected back through the interferometer input (e.g., the signals reflected from the porchswing mirror through the beam splitters and from the dynamic alignment module via beam splitter 44 each include approximately one-quarter of the initial laser signal energy), while the remaining portion of the laser signal impacts fold mirror 52 for direction toward the telescope and detectors for processing (e.g., the signals reflected from the porchswing mirror via beam splitter 46 and from the dynamic alignment module through the beam splitters each include approximately one-quarter of the initial laser signal energy).

The arrangement of beam splitters 44, 46 within interferometer 40 (e.g., in a substantially non-parallel fashion) prevents certain reflections within the system from affecting the reflection component of the detected signal described above (e.g., the detected signal includes the desired signal component A and reflected signal components B and C as illustrated in FIG. 2). Generally, multiple reflections occurring within the system are directed in different directions. One of the reflections occurs at detector 66 with the laser signal being reflected from the detector surface (e.g., illustrated as signal component B within FIG. 2). This reflected signal travels back through optics unit 55 and into interferometer 40, where the interferometer reflects the signal back through the optics unit toward the detector. Another reflection (e.g., illustrated as signal component C within FIG. 2) occurs at the input of interferometer 40, where approximately one-half of the energy of the laser signal from the scene select module or collimator enters the interferometer, while the remaining portion is reflected back as described above and traverses the scene select module and collimator to the integrating sphere. When the signal reaches integrating sphere 18, a small portion of the laser signal may be reflected back through the collimator and scene select module into the interferometer. In addition, reflections occur within the interferometer and telescope 60 of optics unit 55. Thus, the multiple reflections include those produced toward the system input (e.g., signal component C as viewed in FIG. 2)), those produced toward the system output (e.g., signal component B as viewed in FIG. 2) and those occurring within the interferometer and telescope. Beam splitters 44, 46 are slightly wedged and basically prevent the reflections occurring within the interferometer and telescope from combining with the other reflections (e.g., signal components B and C as viewed in FIG. 2).

Porchswing mirror 48 is manipulable to perform a linear or distance movement toward or away from beam splitters 44, 46. Accordingly, the interferometer typically further includes position actuator 45 (e.g., motor, linkage, etc.) to enable movement of the porchswing mirror. This motion enables interferometer 40 to produce an amplitude modulated laser signal with a sinusoidal intensity as a function of the linear motion of porchswing mirror 48. The distance between the porchswing mirror and beam splitters controls the intensity of or modulates the laser signal. In other words, the interferometer produces a signal with a sinusoidally changing optical flux. The motion of porchswing mirror 48 adjusts the optical path difference of the interferometer (e.g., the difference of the distances between the beam splitters and porchswing mirror 48 and between the beam splitters and dynamic alignment module 42) and is controlled by a different laser source as described below. These changes in the optical path difference modulate the photon flux to produce the sinusoidal waveform. The optical path difference is further utilized to control sampling of the detected signal as described below. The laser optical power can be adjusted so that the interferometer amplitude modulation of the laser signal produces a detected sinusoidal signal magnitude equal to the peak to peak interferogram level normally processed through a detector in any given application. Different combinations of sinusoidally modulated and unmodulated photon flux may be synthesized by tilting the alignment of the interferometer mirrors.

System 100 further includes a metrology controller 90 to control movement of the porchswing mirror for modulation of the laser signal and to trigger sampling of the detected signal. The metrology controller typically includes a metrology laser unit 92, a metrology laser detector 94, an amplifier 96, a zero crossing detector 98 and a mirror servo-controller 99. Metrology laser unit 92 may be implemented by any conventional or other laser or light source and emits a metrology laser signal into the optical path of system 100 to enable controller 90 to control movement of porchswing mirror 48. Since the metrology laser signal emitted by metrology laser unit 92 is utilized to trigger sampling, the emitted signal includes a frequency substantially greater than that of the measurement laser signal produced by laser unit 12. Generally, the frequency of the metrology laser signal is greater than that of the measurement laser signal by at least a factor of four in order to satisfy the Nyquist rate (e.g., the sampling frequency utilized is at least twice that of the signal being sampled) and accommodate the measurement laser signal harmonics containing the non-linearity component. By way of example only, the metrology laser signal has a wavelength of approximately 1.5 um providing a frequency exceeding that of the measurement laser signal by a factor of approximately seven. By using both up going and down going metrology laser zero crossings, another factor of two oversampling can be achieved yielding a total oversampling of fourteen in this example.

Metrology laser unit 92 projects the metrology laser signal onto a metrology reflector 34 disposed within the system signal path between scene select module 30 and interferometer 40. The metrology reflector may be implemented by any conventional or other reflecting devices (e.g., mirror, etc.) and directs the metrology laser signal along the system signal path into interferometer 40. The metrology laser signal is modulated by and traverses the interferometer (e.g., the metrology laser signal path through the interferometer is indicated by the bold or thick lines in FIG. 2) in substantially the same manner described above for the measurement laser signal.

A path reflector 36 is disposed in the signal path between the interferometer and fold mirror 52 to direct a portion of the modulated signal from the interferometer, including the measurement and metrology laser signal portions, to metrology laser detector 94. The path reflector may be implemented by any conventional or other reflecting devices (e.g., mirror, etc.). Detector 94 may be implemented by any conventional or other detector and detects the modulated metrology laser signal.

The detected metrology laser signal is amplified by amplifier 96 and processed by zero crossing detector 98 to detect the presence of a zero crossing. A zero crossing occurs when the amplitude of the sinusoidal metrology laser signal changes between a positive and negative value or vice versa (e.g., crosses a zero amplitude value). The amplifier and zero crossing detector may be implemented by any conventional or other devices (e.g., circuitry, amplifiers, processors, etc.). The detected zero crossings are utilized by mirror servo-controller 99 to control position actuator 45 to move porchswing mirror 48 and to enable sampling of the laser signal detected by detector 66. In particular, metrology controller 90 controls movement of porchswing mirror 48 based on the metrology laser signal wavelength. When the porchswing mirror moves a distance corresponding to a full wavelength of the metrology laser signal, a zero crossing is detected by zero crossing detector 98. The zero crossing detector generates a zero crossing signal indicating detection of a zero crossing. The detected zero crossings or zero crossing signals are utilized by mirror servo-controller 99 to control movement of porchswing mirror 48 via position actuator 45. Specifically, the position actuator moves or sweeps porchswing mirror 48 at a relatively constant rate and in a linear fashion toward and away from beam splitter 46 during the non-linearity measurement. The sweep rate is generally selected to be sufficient to attain a reasonable frequency for the desired component (e.g., signal component A as viewed in FIG. 2) of the measurement laser signal (e.g., approximately 10 KHz) detected by detector 66. The quantity of zero crossings detected (e.g., zero crossing signals received) within a particular time interval indicates the rate or speed of the porchswing mirror. The mirror servo-controller adjusts the rate of the porchswing mirror sweep based on the detected zero crossings to maintain a substantially constant rate of motion (e.g., nominal value +/−1%) during the non-linearity measurement. The metrology laser signal, in effect, is utilized by the metrology controller to form a feedback loop to control the porchswing mirror motion.

Zero crossing detector 98 further triggers sampling of the detected laser signal by an A/D converter 74 (FIG. 2) in response to detection of zero crossings as described below. If the porchswing mirror position is between zero crossings, interpolation of the porchswing mirror distance is required which introduces non-linearity during the porchswing mirror motion or sweep. Thus, the present invention approach of sampling in response to a zero crossing ensures that control of the porchswing mirror is uniform and free of non-linearity distortion. Further, sampling based on the detected zero crossings of the metrology laser signal guarantees that the amplitude modulation of the measurement laser signal photon flux is perfectly sinusoidal since sampling occurs at the proper time based on the position of the interferometer porchswing mirror. Since the interferometer does not introduce non-linearity, the non-linearity component within the harmonic content of the sampled measurement laser signal must be produced in the detector and/or the processing unit following the detector.

Fold mirror 52 is preferably implemented by a conventional folding type mirror and directs the modulated measurement laser signal from interferometer 40 into optics unit 55. Alternatively, the system may be employed without fold mirror 52, where interferometer 40 may direct the modulated laser signal into the optics unit. The optics unit includes a telescope 60, beam splitters 62 and optical filters 64. Telescope 60 is preferably implemented by a conventional reflecting type telescope and focuses the modulated laser signal for detection by detectors 66. By way of example only, telescope 60 includes an input concave mirror 61, a secondary flat mirror 63, a primary concave mirror 65, a lens 67 and an output flat mirror 69. The modulated measurement laser signal initially impacts input concave mirror 61 that reflects the signal in a converging fashion onto secondary mirror 63 including dimensions substantially less than those of input concave mirror 61. The secondary mirror is disposed at or near the focal point of input concave mirror 61 and directs the signal in a diverging fashion onto primary concave mirror 65 including dimensions greater than those of the secondary and input concave mirrors. The primary concave mirror reflects the modulated measurement signal received from the secondary mirror in a converging fashion through lens 67 to output mirror 69. The lens directs the measurement laser signal in a converging fashion to output mirror 69 for reflection toward detectors 66. The telescope may alternatively be implemented by any conventional or other telescopes or optical devices and may include any conventional or other optical components (e.g., mirrors, lenses, etc.) arranged in any fashion.

The modulated measurement laser signal from telescope 60 is directed toward detectors 66. By way of example only, system 100 includes three sets of detectors 66. The system may perform non-linearity measurements for each detector within a detector set simultaneously, provided that all detectors respond to the same wavelength of the laser source. However, system 100 may employ any quantity of detector sets with any quantity of detectors in each set, such as two dimensional (e.g., n×m) detector arrays. The modulated laser signal from telescope 60 is directed toward beam splitters 62 that distribute appropriate band portions of the modulated signal to the corresponding detector sets. System 100 may alternatively be utilized without beam splitters 62 when a single detector set or detector is employed. In this case, the telescope directs the modulated laser signal toward the detectors.

Each detector set is associated with optical band pass filters 64 that receive the laser signal from beam splitters 62 (or telescope 60). The optical filters eliminate any possibility of significant optical energy emitted by laser source 10 from being detected by the detectors in the region of interest for the non-linearity measurement. Optical filters 64 are sub-octave to prevent any non-linearities or excess signal energy from laser source 10 to double in frequency and fall outside the optical filter band, thereby removing that energy prior to detection of the laser signal by detectors 66. The optical filters and beam splitters may be implemented by any conventional or other optical devices (e.g., filters, lenses, etc.), where the filters may pass or filter any desired bands.

Detectors 66 receive the modulated laser signal from optical filters 64 and are coupled to processing unit 70. The processing unit samples and processes the detected signal to determine detector non-linearity as described below. The processing unit includes filter and amplifier unit 72, analog to digital (A/D) converter 74, a memory 76 and a processor 80. The filter and amplifier unit receives the detected signal from detector 66 and includes an amplifier and low pass filter to amplify and extract the desired signal components. The filtered signal is directed to A/D converter 74 for conversion to a digital signal or value. Converter 74 samples the filtered signal in accordance with zero crossing detections or signals from metrology controller 90 as described above. This sampling is performed synchronous to the mechanical porchswing mirror position to assure sinusoidal response regardless of the actual mechanical mirror movement rate. This near perfect sinusoid is recovered by the metrology controller triggering converter 74 to sample detector response in accordance with each zero crossing detection. The amplifier, low pass filter and converter may be implemented by any conventional or other devices (e.g., chip, circuitry, logic, etc.).

A finite quantity of sampled digital signals are stored in memory 76 for processing by processor 80. The memory may be implemented by any conventional or other storage device (e.g., memory, processor memory, etc.). The processor is preferably implemented by a conventional personal computer, but may be implemented by any type of processing system, processor or circuitry. The processor includes various modules to process the sampled digital signals stored in memory 76. These modules may be implemented by any software and/or hardware (e.g., circuitry, logic, etc.) modules or units. In particular, the processor includes an FFT module 82, a subtraction module 84 and a double pass removal module 86. The FFT module windows the sample set and performs a Fast Fourier Transform. By way of example only, the FFT module employs a conventional Blackman-Harris windowing technique. However, any conventional or other windowing technique may be employed, provided that spectral sidelobes resulting from using the window function in combination with the FFT result in negligible signal contribution at the second harmonic of the detected laser test signal. Subtraction module 84 removes background energy from the results of the FFT module, while the double pass removal module analyzes the data from the subtraction module to identify the signal component attributed to detector non-linearity as described below. The system is capable of measuring detector non-linearity to a 20 ppm accuracy (e.g., 94 dB dynamic range or 0.002%).

Referring to FIGS. 3A–3C, the signal sampled from detector 66 is illustrated within the frequency domain. A signal detected by detector 66 includes a desired signal component within the first harmonic (e.g., illustrated as signal component A in FIG. 3A) and a multiple reflection component (e.g., illustrated as signal components B and C in FIG. 3B) within the second harmonic respectively corresponding to the reflections at the detector and interferometer as described above. Signal component A represents the laser signal modulated by the interferometer and in the form of a sinusoidal wave including an approximate frequency of 10.4 KHz in this example. The frequency of this signal depends on the laser source utilized and the rate that the interferometer sweeps or moves porchswing mirror 48. The sweep rate is generally selected to be sufficient to attain a reasonable frequency for the detected laser signal (e.g., approximately 10 KHz for signal component A), while the processing unit has to be broad enough in frequency to process all the harmonics of the detected laser signal (e.g., 20 KHz for the second harmonic including signal components B and C). Signal components A, B and C may be expressed as follows:

$$Ⓐ = a \cdot [L_L(\sigma_L) + L_{BB}(\sigma)] \cdot \tau_1(\sigma) \cdot \tau_2(\sigma) \cdot A\Omega \cdot \frac{m(\sigma) \cdot \tilde{n}(\sigma)}{2} \cdot \cos(2\pi \upsilon \sigma) \quad \text{(Equation 1)}$$

$$Ⓑ = -a \cdot [L_L(\sigma_L) + L_{BB}(\sigma)] \cdot \tau_1^3(\sigma) \cdot \tau_2(\sigma) \cdot \Gamma_1(\sigma) \cdot A\Omega \cdot \frac{m^2(\sigma) \cdot \tilde{n}^2(\sigma)}{4} \cdot \cos^2(2\pi \upsilon \sigma) \quad \text{(Equation 2)}$$

$$Ⓒ = -a \cdot [L_L(\sigma_L) + L_{BB}(\sigma)] \cdot \tau_1(\sigma) \cdot \tau_2^3(\sigma) \cdot \Gamma_2(\sigma) \cdot A\Omega \cdot \frac{m^2(\sigma) \cdot \tilde{n}^2(\sigma)}{4} \cdot \cos^2(2\pi \upsilon \sigma) \quad \text{(Equation 3)}$$

When the detected signal is processed by processing unit 70, an additional component $K_d * A * A$ is produced (FIG. 3C) in the sampled signal (e.g., from A/D converter 74) that corresponds to the detector and/or system non-linearity. The sampled signal, $S_{A/D}$, including the desired (signal component A), reflection (signal components B and C) and non-linearity (signal component $K_d * A * A$) components from A/D converter 74 may be expressed as follows.

$$S_{A/D} = [Ⓐ + Ⓑ + Ⓒ + K_d * Ⓐ * Ⓐ] \cdot \rho_d(\sigma) \cdot \tilde{M}(\upsilon \sigma) \quad \text{(Equation 4)}$$

where the parameters for above Equations 1–4 are as follows:

$L_L(\sigma_L)$ represents the radiance from the laser source that exercises system dynamic range in units of Watt/centimeter$^2$/steradian/centimeter$^{-1}$ (W/cm$^2$/sr/cm$^{-1}$);

$L_{BB}(\sigma_L)$ represents the radiance background from the source at laser wavenumber $\sigma_L$ in units of Watt/centimeter$^2$/steradian/centimeter$^{-1}$ (W/cm$^2$/sr/cm$^{-1}$);

$\Gamma_1(\sigma_L)$ represents the reflection coefficient of the source at laser wavenumber $\sigma_L$ (unitless);

$\Gamma_2(\sigma_L)$ represents the reflection coefficient of the detector focal plane at laser wavenumber $\sigma_L$ in units of Watt/centimeter$^2$/steradian/centimeter$^{-1}$ (W/cm$^2$/sr/cm$^{-1}$);

$\tau_1(\sigma)$ represents the optical transmission of the scene select module at laser wavenumber $\sigma$ (unitless);

$\tau_2(\sigma)$ represents the optical transmission of the optics unit at laser wavenumber $\sigma$ (unitless);

$A\Omega$ represents the optical throughput of the system in units of steradian centimeter$^2$ (sr cm$^2$);

$\upsilon$ represents the interferometer optical path difference rate in units of rate centimeter/second (cm/sec);

$m(\sigma)$ represents the interferometer modulation efficiency at wavenumber $\sigma$ in units of centimeter/second (cm/sec);

$\tilde{n}(\sigma)$ represents the complex interferometer beam splitter efficiency at wavenumber $\sigma$ in units of centimeter/second (cm/sec);

$\rho_d(\sigma)$ represents the detector responsivity at wavenumber $\sigma$ in units of Ampere/Watt (A/W);

$K_d$ represents the detector second order non-linearity coefficient in units of Ampere$^{-1}$ (A$^{-1}$);

$\tilde{M}(\upsilon\sigma)$ represents the complex amplifier and filter electronic gain at electrical frequency $\upsilon\sigma$ in units of Volt/Ampere (V/A); and a represents the laser power attenuation (unitless) (e.g., a=1 for measurement at maximum power, and a<1 for a measurement at reduced laser power).

The parameters $\Gamma_1(\sigma_L)$, $\Gamma_2(\sigma_L)$ and $K_d$ representing the reflection and non-linearity signal components are determined from measurements performed by the system as described below.

The multiple reflection component produces a signal in the second harmonic of the sampled signal coincident with (e.g., or within the same bin location of an FFT as) the non-linearity component within that harmonic, except that the reflection component is one-hundred eighty degrees out of phase with the non-linearity component (FIGS. 3B and 3C). When the signals are processed through an FFT, a second harmonic that is predominantly one-hundred eighty degrees out of phase with the first harmonic indicates the reflection component. Conversely, if the second harmonic is in-phase with the desired laser signal, this indicates the non-linear component.

In order to determine detector non-linearity, the multiple reflection component is discerned from the non-linearity component to enable determination of detector non-linearity. Accordingly, the components may be discerned based on properties relating to the phase difference and laser intensity. Since the reflection and non-linear components typically combine (e.g., the signals subtract), laser intensity is primarily utilized to identify the components in the sampled signal. In particular, if the laser energy is reduced, the multiple reflection component in the FFT bin is also reduced by the same proportion as the laser signal. For example, if the laser energy is reduced by a factor of two, the multiple reflection component is reduced by a factor of two. However, the non-linearity component is reduced by a square of the proportion of the laser signal (e.g., based on the squared relation in the non-linearity component expression, $K_d*A*A$). By way of example, if the laser energy is reduced by a factor of two, the non-linearity component is reduced by a factor of four.

Figure 4:
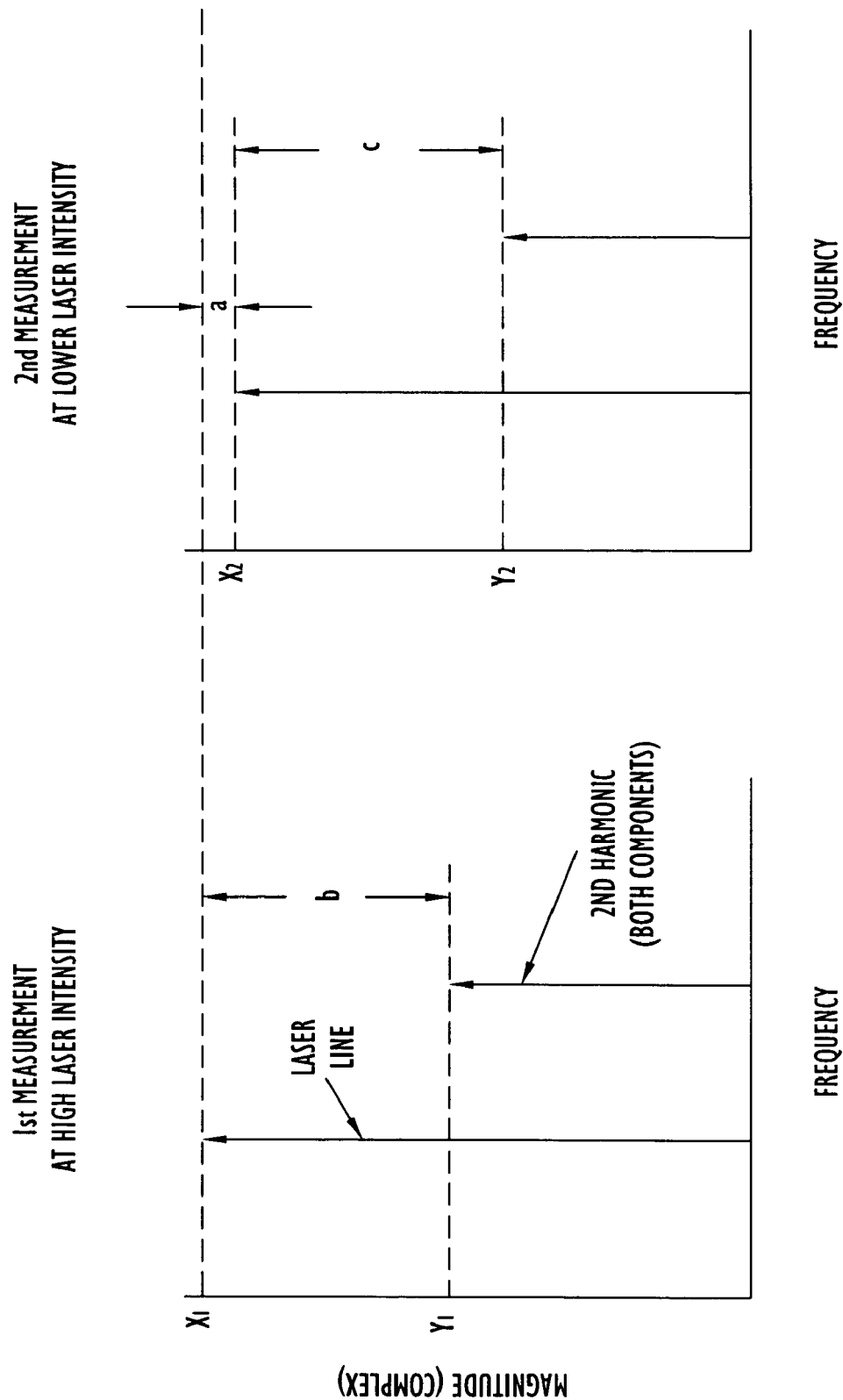
FIG. 4 is a set of graphical illustrations of the relationships between detector measurements and the parameters utilized to determine detector non-linearity according to the present invention.

Since the change in the non-linearity component differs from the reflection component, the components may be identified by two measurements each with a different laser intensity. This provides two equations with two unknowns, thereby enabling identification of the reflection and non-linearity components. Referring to FIG. 4, a first measurement is performed with the laser source at a maximum level. The desired portion of the sampled signal, $X_1$, may be expressed in terms of the above parameters as follows.

$$X_1 = [L_L(\sigma_L) + L_{BB}(\sigma)] \cdot \tau_1(\sigma) \cdot \qquad \text{(Equation 5)}$$
$$\tau_2(\sigma) \cdot A\Omega \cdot \frac{m(\sigma) \cdot \tilde{n}(\sigma)}{2} \cdot \rho(\sigma) \cdot \tilde{M}(\upsilon\sigma)$$

The second harmonic of the sampled signal, $Y_1$, includes the reflection and non-linearity components and may be expressed in terms of the above parameters as follows.

$$Y_1 = \qquad \text{(Equation 6)}$$

$$X_1 b = X_1^2 \cdot K_d - X_1 \cdot \frac{m(\sigma) \cdot \tilde{n}(\sigma)}{4} \cdot [\Gamma_1(\sigma) \cdot \tau_1^2 + \Gamma_2(\sigma) \cdot \tau_2^2]$$

where the first term, $X_1^2 \cdot K_d$, represents the non-linearity component (e.g., $K_d*A*A$) and the remaining term represents the reflection components (e.g., signal components B and C).

A second measurement is performed with the laser source at a reduced level (e.g., 0.7>a>0.3 or a reduction of 30%, 50%, etc.). The desired portion of the sampled signal, $X_2$, may be expressed in terms of the above parameters as follows.

$$X_2 = a \cdot [L_L(\sigma_L) + L_{BB}(\sigma)] \cdot \tau_1(\sigma) \cdot \qquad \text{(Equation 7)}$$
$$\tau_2(\sigma) \cdot A\Omega \cdot \frac{m(\sigma) \cdot \tilde{n}(\sigma)}{2} \cdot \rho(\sigma) \cdot \tilde{M}(\upsilon\sigma)$$

The second harmonic of the sampled signal, $Y_2$, includes the reflection and non-linearity components and may be expressed in terms of the above parameters as follows.

$$Y_2 = X_1 ac = \qquad \text{(Equation 8)}$$
$$a^2 \cdot X_1^2 \cdot K_d - a \cdot X_1 \cdot \frac{m(\sigma) \cdot \tilde{n}(\sigma)}{4} \cdot [\Gamma_1(\sigma) \cdot \tau_1^2 + \Gamma_2(\sigma) \cdot \tau_2^2]$$

where $X_1^2 \cdot K_d$ represents the non-linearity component (e.g., $K_d*A*A$) and the remaining term represents the reflection components (e.g., signal components B and C). Equations 5–8 may be derived by inserting Equations 1–3 into Equation 4 described above.

The measured signal, $X_1$, represents the magnitude of the laser line, while the signal, $Y_1$, represents the magnitude of the second harmonic within the first measurement. Similarly, the measured signal, $X_2$, represents the magnitude of the laser line, while the signal, $Y_2$, represents the magnitude of the second harmonic within the second measurement. The second harmonics include the non-linearity and reflection components as described above. The parameters a, b, c indicate relationships between the signals as illustrated in FIG. 4. Parameter a is the laser intensity attenuation as described above and represents the relationship between the desired signals at different intensities (e.g., signals $X_1$ and $X_2$). This parameter may be expressed as the ratio of signals $X_1$ and $X_2$:

$$a = X_2/X_1. \qquad \text{(Equation 9)}$$

Parameter b represents the relationship between the desired and harmonic signals within the first measurement (e.g., signals $X_1$ and $Y_1$) and may be expressed as the ratio of signals $Y_1$ and $X_1$:

$$b = Y_1/X_1. \qquad \text{(Equation 10)}$$

Parameter c represents the relationship between the desired and harmonic signals within the second measurement (e.g., signals $X_2$ and $Y_2$) and may be expressed as the ratio of signals $Y_2$ and $X_2$:

$$c = Y_2/X_2. \qquad \text{(Equation 11).}$$

The parameter relationships described above (e.g., Equations 9–11) may be utilized with above Equations 5–8 to derive expressions for the reflection and non-linearity terms. The resulting magnitudes for the reflection and non-linearity components may be expressed in terms of parameters a, b and c as follows.

$$\text{Non-Linearity Magnitude} = \left[\frac{b-c}{1-a}\right];$$ (Equation 12)

$$\text{Double Pass or Reflection Magnitude} = \left[\frac{-c}{1-a}\right].$$ (Equation 13)

These expressions (e.g., Equations 9–13) represent complex calculations (e.g., operations with complex numbers) involving real and imaginary components, where the signals $X_1$, $Y_1$, $X_2$ and $Y_2$ are expressed as complex values from FFT module 82 and subtraction module 84 (e.g., with the magnitude and phase) that yield complex results for parameters a, b, c (e.g., Equations 9–11). The parameters are utilized within Equations 12–13 to produce complex results for the respective components, where the magnitudes of these results may be expressed as follows.

$$\text{Magnitude} = \sqrt{\text{real}^2 + \text{imaginary}^2}$$ (Equation 14)

where real and imaginary respectively represent the real and imaginary components of the complex results.

System 100 performs measurements with different laser intensities as described below to determine parameters a, b and c. The system utilizes the parameters to perform complex arithmetic and determine the non-linearity and reflection component magnitudes (e.g., Equations 12–13) so that these overlapping harmonics can be uniquely identified and separated. The magnitude values represent a ratio of the second harmonic to the fundamental frequency for the respective reflection and non-linearity components. Thus, the resulting magnitude equations are relatively simplistic, where the above parameters for Equations 1–8 substantially cancel out in the derivation and yield a precise measurement technique without requiring precise calibration of laser source 10, interferometer 40 or optics module 55. Other techniques employing harmonic analysis with a broadband optical source, such as the LED harmonic analysis technique described above, are significantly more difficult than the present invention since the above parameters do not cancel out and the linearity of the LED modulation must be precisely calibrated for sinusoidal optical modulation.

Figure 5:
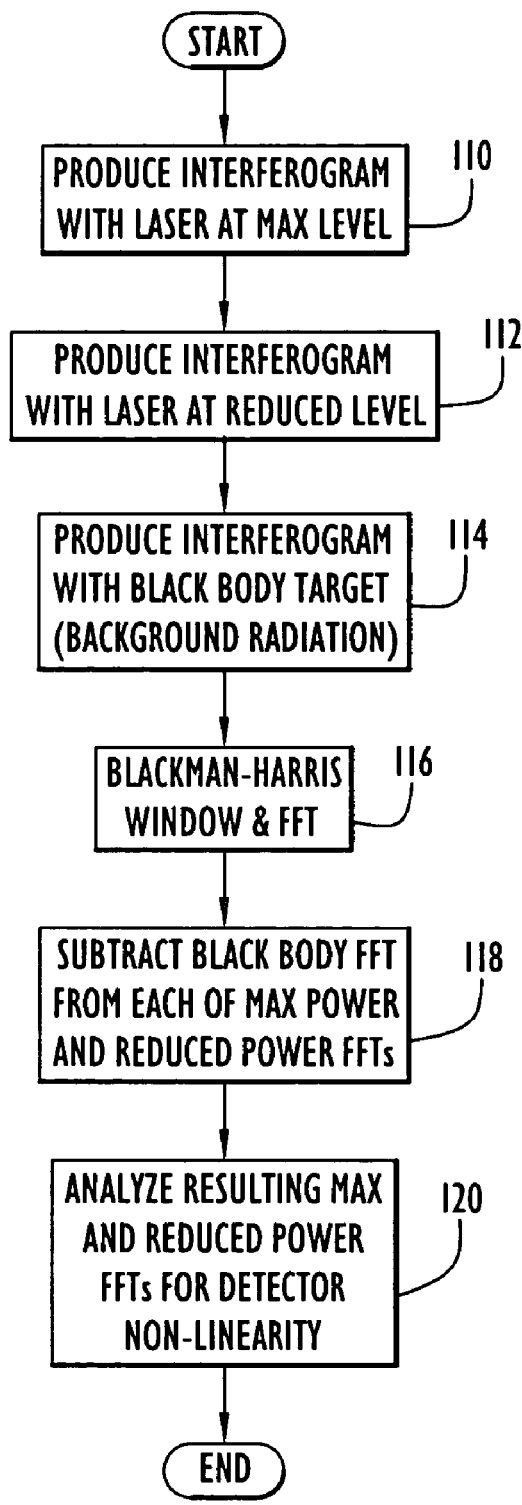
FIG. 5 is a procedural flow chart illustrating the manner in which the system determines detector non-linearity according to the present invention.

The manner in which detector non-linearity may be measured according to the present invention is illustrated in FIG. 5. Specifically, system 100 (FIGS. 1–2) is utilized to record a measurement at step 110 with laser source 10 at a maximum level that detector 66 can accommodate. Metrology controller 90 controls porchswing mirror 48 to modulate the laser signal and triggers A/D converter 74 to sample data based on the mirror position as described above. The sampled data from the measurement is stored in memory 76. The measurement records information for only a portion of the porchswing mirror sweep, preferably on the order of approximately the initial forty-five percent of the sweep prior to encountering the zero optical path difference of interferometer 40. Basically, the porchswing mirror sweeps (e.g., moves linearly with respect to the beam splitters within the interferometer as described above) from positive to negative optical path differences within the interferometer. When the porchswing mirror enters a position having a zero optical path difference, a spike occurs which may provide additional energy that saturates the detector under test and processing unit 70. Accordingly, the system captures information from the initial portion of the sweep (e.g., prior to the occurrence of the spike) in order to avoid the effects of the zero optical path difference spike. In addition, the exclusion of the spike enhances the signal to noise ratio, thereby enabling measurements with enhanced accuracy.

System 100 is utilized to record a second measurement at step 112 with laser source 10 at a reduced level (e.g., 30% reduction). The metrology controller controls porchswing mirror 48 to modulate the laser signal and triggers A/D converter 74 to sample data based on the mirror position as described above. The second measurement is stored in memory 76. The measurement records information for only a portion of the porchswing mirror sweep as described above. System 100 may be utilized to record a third measurement at step 114, where the system looks at cold black body target 35 to measure background radiance of interferometer 40, scene select module 30 and optics module 55. This is accomplished by adjusting or rotating the position of scene select module 30 as described above. The third measurement and associated processing described below are optional and may be used to enhance accuracy. The third measurement is stored in memory 76.

Once the measurements are stored in memory 76, processor 80 performs Blackman-Harris windowing and a Fast Fourier Transform for the measurements at step 116 via FFT module 82. The windowing enables the present invention to attain an enhanced dynamic range for the measurements, preferably on the order of 100 dB. The FFT of each measurement provides a series of frequency bins each with the corresponding magnitude and phase of the signal. The size or quantity of points within the FFT is based on the quantity of samples collected and the movement of the porchswing mirror. Preferably, the size of the FFT is sufficient to accommodate each sample collected during the porchswing mirror sweep (e.g., the initial forty-five percent of the sweep as described above). If the black body measurement is employed, the FFT associated with that measurement is algebraically subtracted from each of the first and second measurements (e.g., the measurements at maximum and reduced laser intensity) at step 118 by processor 80 via subtraction module 84. This essentially removes background radiance from the first and second measurements. Basically, the system emits its own energy which is detected by detector 66. This background energy is present within the first and second measurements. The third measurement is a measure of the background energy and is subtracted or removed from the first and second measurements to prevent the background energy from affecting the non-linearity determination.

The resulting FFTs of the first and second measurements (with or without background energy removed) are analyzed by processor 80, via double pass module 86, to identify the non-linearity component at step 120. In particular, the FFTs of the first and second measurements are utilized to determine the above-described parameters a, b and c (e.g., Equations 9–11) based on the magnitude and phase of the desired signals (e.g., signals $X_1$ and $X_2$) and corresponding second harmonics (e.g., signals $Y_1$ and $Y_2$, including the reflection and non-linearity components) within the FFT results. The parameters enable determination of the non-linearity and reflection component magnitudes as described above (e.g., Equations 12–13). The magnitude of the non-linearity component indicates the ratio of the second harmonic to the fundamental frequency for that component. The magnitude of the non-linearity component may be converted to any desired scales or units to indicate the non-linearity of the detector. For example, the magnitude may be divided by one-hundred to indicate detector non-linearity in terms of a percentage. The present invention provides non-linearity measurement with enhanced accuracy, typically on the order of twenty parts per million (e.g., the magnitude of the fundamental to the noise floor is on the order of 100 dB).

It will be appreciated that the embodiments described above and illustrated in the drawings represent only a few of the many ways of implementing a method and apparatus for measurement of optical detector linearity.

The system may include any quantity of any desired optical and other components (e.g., laser source, optics unit, interferometer, processing unit, detector, etc.) arranged in any fashion to conduct the measurement. The laser unit may be implemented by any quantity of any conventional or other laser, light or other energy source to produce signals in any desired frequency (or wavelength) band or range. The integrating sphere may be of any quantity, shape or size, may be implemented by any conventional or other optical device (e.g., sphere, reflectors, mirrors, lenses, etc.) and may be disposed at any suitable location or orientation within the system. The optical attenuator may be of any quantity, shape or size, may be implemented by any conventional or other optical device (e.g., lens, etc.) and may produce any desired flux level. The shutter attenuator may be of any quantity, shape or size, may be implemented by any conventional or other optical device (e.g., lens, etc.) and may produce any desired intensity level. The attenuators may be disposed at any location or orientation within the system.

The collimator may be of any quantity, shape or size, may be implemented by any conventional or other optical device (e.g., collimator, reflectors, mirrors, lenses, etc.) and may be disposed at any suitable location or orientation within the system. The collimator may expand the signal to any desired aperture. Alternatively, the system may employ a larger integrating sphere and a more powerful laser and be utilized without the collimator.

The scene select module may be of any quantity, shape or size, may be implemented by any conventional or other optical device (e.g., reflectors, mirrors, lenses, etc.) and may be disposed at any suitable location or orientation within the system. The scene select module may be positioned in any quantity of positions to direct any optical signals in any desired direction. The cold black body target may be implemented by any type of target or other object and may be disposed at any suitable location relative to the scene select module and/or system.

The interferometer may be of any quantity, shape or size, may be implemented by any conventional or other optical device (e.g., interferometer, reflectors, mirrors, lenses, telescope, etc.) and may be disposed at any suitable location or orientation within the system. The interferometer components (e.g., dynamic alignment module, beam splitters, porchswing mirror, etc.) may be of any quantity, shape or size, may be implemented by any conventional or other optical devices (e.g., reflectors, mirrors, lenses, etc.) and may be disposed at any suitable location or orientation within the interferometer. The components may be arranged or manipulated in any fashion to achieve any desired modulation (e.g., the dynamic alignment module and/or porchswing mirror may be tilted, the rate and/or motion of the porchswing mirror may be controlled in any fashion, etc.). The porchswing mirror may move in any desired directions and at any desired rate to modulate the signal. The position actuator may be of any quantity, may be disposed at any suitable location and may be implemented by any conventional or other actuator (e.g., motor, linkage, etc.) to sweep the porchswing mirror.

The metrology controller may be disposed at any suitable location within the system. The metrology controller components (e.g., detector, amplifier, zero crossing detector, mirror servo-controller, etc.) may be implemented by any quantity of any conventional or other devices (e.g., amplifier, detectors, processor, circuitry, software modules, etc.) performing the described functions and may be arranged in any fashion. The metrology laser unit may be implemented by any quantity of any conventional or other laser, light or other energy source to produce signals in any desired frequency (or wavelength) band or range suitable to sample the measurement signal. The metrology and path reflectors may be of any quantity, shape or size, may be implemented by any conventional or other optical device (e.g., reflectors, mirrors, lenses, etc.) and may be disposed at any suitable location or orientation within the system. The amplifier may amplify the signal to any desired level. The zero crossing detector may generate any type of signal (e.g., digital, analog, interrupt, etc.) to indicate a zero crossing for control of the porchswing mirror and/or sampling. The metrology detector may be of any quantity, shape or size, may detect any type of energy signal (e.g., laser, light, etc.) of any desired frequency (or wavelength) band or range and may be disposed at any desired location or orientation within the metrology controller and/or system.

The fold mirror may be of any quantity, shape or size, may be implemented by any conventional or other optical device (e.g., reflectors, mirrors, lenses, etc.) and may be disposed at any suitable location or orientation within the system. The system may alternatively be utilized without the fold mirror, where the measurement signal may be directed to the telescope from the interferometer. The telescope may be of any quantity, shape or size, may be implemented by any conventional or other optical device (e.g., telescope, reflectors, mirrors, lenses, etc.) and may be disposed at any suitable location or orientation within the system. The telescope components (e.g., input concave mirror, secondary flat mirror, primary concave mirror, lens, output flat mirror, etc.) may be of any quantity, shape or size, may be implemented by any conventional or other optical devices (e.g., reflectors, mirrors, lenses, etc.) and may be disposed at any suitable location or orientation within the telescope.

The detectors may be of any quantity, shape or size, may be arranged into any quantity of sets with each set having any quantity of detectors, may detect any type of energy signal (e.g., laser, light, etc.) of any desired frequency (or wavelength) band or range and may be disposed at any desired location or orientation within the system. The optical filters may be of any quantity, shape or size, may be implemented by any type of optical or filter device (e.g., filter, lens, etc.), may filter or pass any desired frequency (or wavelength) band or range and may be disposed at any desired location or orientation within the system. The beam splitters associated with the detectors may be of any quantity, shape or size, may be implemented by any type of optical device (e.g., filter, lens, etc.), may distribute any desired frequency (or wavelength) band or range to the detectors and may be disposed at any desired location or orientation within the system. The system may be implemented without these beam splitters in the case of a single detector or detector set including detectors detecting signals within a common band.

The processing unit may be disposed at any suitable location within the system. The processing unit components (e.g., filter and amplifier, A/D converter, memory, processor, etc.) may be implemented by any quantity of any conventional or other devices (e.g., amplifier, filters, processor, circuitry, software modules, etc.) performing the described functions and may be arranged in any fashion. The filter may be implemented by any quantity of any type of filter (e.g., high pass, low pass, band pass, etc.) and pass or filter any desired frequency (or wavelength) band or range. The amplifier may amplify the signal to any desired level. The A/D converter may utilize any quantity of bits for any desired resolution and sample values in response to any desired conditions (e.g., zero crossing, timed or periodic sampling, etc.). The memory may be implemented by any quantity of any type of storage device (e.g., memory device, RAM, cache memory, processor memory, etc.). The processor may be implemented by any conventional or other computer system (e.g., personal computer, PDA, laptop, etc.), microprocessor, controller or circuitry to perform the functions described herein (e.g., windowing, FFT, subtraction, double pass removal, etc.), while any quantity of processors or processing devices or circuitry may be employed where the processor functions may be distributed in any fashion among any quantity of hardware and/or software modules, processors or other processing devices or circuits. The software for the processor may be implemented in any suitable computer language, and could be developed by one of ordinary skill in the computer and/or programming arts based on the functional description contained herein and the flow chart and diagrams illustrated in the drawings. Further, any references herein of software performing various functions generally refer to processors performing those functions under software control. The software and/or algorithms described above and illustrated in the drawings may be modified in any manner that accomplishes the functions described herein.

The FFT may include any desired quantity of points or stages, while the system may employ any conventional or other windowing technique. The cold black body target or background energy measurement may be removed from the other measurements in any desired fashion (e.g., subtraction, weighted scheme, etc.). The resulting magnitudes of the non-linearity and/or reflection components may be converted to any desired scales or units to indicate those components. The measurements may be sampled for any desired portions of the porchswing mirror sweep excluding the zero optical path difference spike (e.g., any initial portion of the sweep prior to the spike and/or any portion of the sweep after the spike, etc.). Alternatively, the total sweep may be sampled with the spike and/or other data removed by any conventional or other processing techniques.

The system may utilize any quantity of measurements at any desired intensities, where the measurements may be combined in any fashion (e.g., weighted scheme, averaged, etc.). The system may utilize any quantity of cold black body target or background radiance measurements, where the measurements may be combined in any fashion (e.g., weighted scheme, averaged, etc.) and removed from the non-linearity measurements in any fashion.

It is to be understood that the present invention is not limited to the applications described herein, but may be utilized for various applications, especially those pertaining to establishing scientific standards for detector linearity and optical test equipment for UV, visible and IR detector characterization. For example, the present invention may be utilized for: test equipment used to characterize detector response linearity over an 94 dB dynamic range by optical excitation methods; calibration of scientific instruments and remote sensors that have optoelectronic detectors; and detector characterization for manufacturers of optoelectronic detectors.

From the foregoing description, it will be appreciated that the invention makes available a novel method and apparatus for measurement of optical detector linearity, wherein detector linearity is measured by identifying signal portions attributed to detector non-linearity based on a harmonic analysis of measurement signals detected by the detector.

Having described preferred embodiments of a new and improved method and apparatus for measurement of optical detector linearity, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A system for measuring linearity of an optical detector comprising:
    an optical energy source to generate an optical measurement signal;
    a modulator including a movable reflector to modulate said optical measurement signal in accordance with a position of said reflector;
    a control unit to control movement of said reflector and determine said reflector position;
    an optics unit to direct said modulated measurement signal to said optical detector; and
    a processing unit coupled to said optical detector to sample said modulated measurement signal detected by said optical detector in accordance with said reflector position and to perform a harmonic analysis of said sampled signal to determine non-linearity of said optical detector.

2. The system of claim 1, wherein said optical energy source includes a laser to generate said optical measurement signal in the form of a laser signal.

3. The system of claim 2, wherein said optical energy source includes an integrating sphere to randomize a phase of said optical measurement signal to produce a uniform optical intensity, wherein said integrating sphere enables variance of optical measurement signal intensity without affecting a reflection component of said sampled signal.

4. The system of claim 3, wherein said optical energy source further includes a collimator to expand said optical measurement signal from said integrating sphere for compatibility with said modulator.

5. The system of claim 2 further including:
    a scene select unit to selectively direct optical signals to said modulator, wherein said optical signals include one of said optical measurement signal from said optical energy source and optical signals from a target object.

6. The system of claim 2, wherein said optics unit includes:
    an optical filter to remove at least one of excess energy and non-linearity from said modulated measurement signal.

7. The system of claim 1, wherein said control unit includes:
    a laser unit to generate a position signal to traverse said modulator and measure said reflector position;
    a detector to detect said position signal from said modulator;
    an amplifier to amplify said detected position signal;

a zero crossing detector to detect transitions of said position signal between positive and negative amplitude values, wherein said transitions indicate positions of said reflector; and a controller to control movement of said reflector in accordance with said detected transitions.

8. The system of claim 7, wherein said processing unit includes:

a filter to amplify and filter said detected signal;

an analog to digital converter to sample said filtered signal in accordance with said detected transitions and to convert said samples to digital values;

a memory to store said digital sample values; and a processor to process said stored digital sample values to determine said optical detector non-linearity.

9. The system of claim 1, wherein said processing unit includes:

a processor including:

a window module to window said sampled modulated measurement signal;

a transform module to transform said windowed signal to a frequency domain; and an analysis module to perform said harmonic analysis for said transformed sampled signal to determine said optical detector non-linearity.

10. The system of claim 9, wherein said optical detector detects at least one optical signal from said optical energy source and detects at least one optical signal from a target object representing ambient energy, and said processor further includes:

a background module to combine transformed signals from said optical energy source and said target object to remove said ambient energy, wherein said analysis module performs said harmonic analysis for said combined signal to determine said optical detector non-linearity.

11. The system of claim 9, wherein:

said optical energy source produces said measurement signal at first and second different intensities, wherein sampled measurement signals each include a desired component, a reflection component associated with reflections of said optical measurement signal within said system and a non-linearity component associated with said optical detector non-linearity;

said reflection and non-linearity components reside within a second harmonic of each sampled signal, wherein said reflection component varies in a first proportion to an intensity of said measurement signal and said non-linearity component varies in a second different proportion to said measurement signal intensity; and said analysis module determines said non-linearity component within said second harmonic of said sampled signals based on said component variations with different measurement signal intensities to produce said optical detector non-linearity.

12. The system of claim 11, wherein said analysis module includes:

a linearity module to determine said optical detector non-linearity in accordance with the following expression:

$$\text{Non-Linearity Magnitude} = \left[\frac{b-c}{1-a}\right];$$

wherein 'a' represents the ratio of the desired signal component at said second intensity to the desired signal component at said first intensity, 'b' represents the ratio of the second harmonic at said first intensity to the desired signal component at said first intensity, and 'c' represents the ratio of the second harmonic at said second intensity to the desired signal component at said second intensity.

13. The system of claim 1, wherein said reflector repeatedly moves through a range of motion to modulate said optical measurement signal, and said processing unit samples said modulated signal for a portion of each reflector movement iteration.

14. The system of claim 13, wherein said processing unit samples said modulated signal for less than half of each reflector movement iteration.

15. A system for measuring linearity of an optical detector comprising:

an optical assembly to generate at least two modulated optical measurement signals with different intensities for detection by said optical detector; and a processing unit coupled to said optical detector to sample and process said modulated measurement signals detected by said optical detector, wherein said sampled signals each include a desired component, a reflection component associated with reflections of said optical measurement signal within said optical assembly and a non-linearity component associated with optical detector non-linearity, said reflection and non-linearity components residing within a second harmonic of each sampled optical measurement signal with said reflection component varying in a first proportion to an intensity of said measurement signal and said non-linearity component varying in a second different proportion to said measurement signal intensity, and wherein said processing unit determines said non-linearity component within said second harmonic of said sampled optical measurement signals based on said component variations with different measurement signal intensities to produce said optical detector non-linearity.

16. The system of claim 15, wherein said optical assembly includes a modulator including a movable reflector to modulate each optical measurement signal in accordance with a position of said reflector, and said processing unit samples each modulated signal in accordance with said reflector position.

17. The system of claim 16, wherein said reflector repeatedly moves through a range of motion to modulate each optical measurement signal, and said processing unit samples each modulated signal for a portion of each reflector movement iteration.

18. The system of claim 15, wherein said optical assembly is configured to enable variance of optical measurement signal intensity without affecting said reflection component of each sampled signal.

19. The system of claim 15, wherein said optical assembly further generates at least one optical signal from a target object representing ambient energy for detection by said optical detector, and said processing unit combines each measurement signal with at least one optical signal from said target object to remove said ambient energy and perform said harmonic analysis for said combined signal to determine said optical detector non-linearity.

20. The system of claim 15, wherein said optical assembly produces said measurement signals at first and second different intensities, and said processing unit includes:

a linearity module to determine said optical detector non-linearity in accordance with the following expression:

$$\text{Non-Linearity Magnitude} = \left[\frac{b-c}{1-a}\right];$$

wherein 'a' represents the ratio of the desired signal component at said second intensity to the desired signal component at said first intensity, 'b' represents the ratio of the second harmonic at said first intensity to the desired signal component at said first intensity, and 'c' represents the ratio of the second harmonic at said second intensity to the desired signal component at said second intensity.

21. A method of measuring linearity of an optical detector comprising:
 (a) generating an optical measurement signal for detection by said optical detector, wherein said optical measurement signal is modulated in accordance with a position of a movable reflector;
 (b) sampling said modulated measurement signal detected by said optical detector in accordance with said reflector position and performing a harmonic analysis of said sampled signal to determine non-linearity of said optical detector.

22. The method of claim 21, wherein said optical measurement signal is in the form of a laser signal.

23. The method of claim 22, wherein step (a) further includes:
 (a.1) varying optical measurement signal intensity without affecting a reflection component of said sampled signal.

24. The method of claim 22, wherein step (a) further includes:
 (a.1) removing at least one of excess energy and non-linearity from said modulated measurement signal.

25. The method of claim 21, wherein step (a) further includes:
 (a.1) generating a position signal to measure said reflector position;
 (a.2) detecting transitions of said position signal between positive and negative amplitude values, wherein said transitions indicate positions of said reflector; and
 (a.3) controlling movement of said reflector in accordance with said detected transitions.

26. The method of claim 25, wherein step (b) further includes:
 (b.1) sampling said modulated measurement signal in accordance with said detected transitions and converting said samples to digital values;
 (b.2) storing said digital sample values; and
 (b.3) processing said stored digital sample values to determine said optical detector non-linearity.

27. The method of claim 21, wherein step (b) further includes:
 (b.1) windowing said sampled modulated measurement signal;
 (b.2) transforming said windowed signal to a frequency domain; and
 (b.3) performing said harmonic analysis for said transformed sampled signal to determine said optical detector non-linearity.

28. The method of claim 27, wherein said optical detector detects at least one generated measurement signal and detects at least one optical signal from a target object representing ambient energy, and step (b.3) further includes:
 (b.3.1) combining transformed signals from said generated signal and said target object to remove said ambient energy and performing said harmonic analysis for said combined signal to determine said optical detector non-linearity.

29. The method of claim 27, wherein step (a) further includes:
 (a.1) generating said measurement signal at first and second different intensities;
 wherein sampled measurement signals each include a desired component, a reflection component associated with reflections of said optical measurement signal and a non-linearity component associated with said optical detector non-linearity;
 wherein said reflection and non-linearity components reside within a second harmonic of each sampled signal, and wherein said reflection component varies in a first proportion to an intensity of said measurement signal and said non-linearity component varies in a second different proportion to said measurement signal intensity; and
step (b.3) further includes:
 (b.3.1) determining said non-linearity component within said second harmonic of said sampled signals based on said component variations with different measurement signal intensities to produce said optical detector non-linearity.

30. The method of claim 29, wherein step (b.3.1) further includes:
 (b.3.1.1) determining said optical detector non-linearity in accordance with the following expression:

$$\text{Non-Linearity Magnitude} = \left[\frac{b-c}{1-a}\right];$$

wherein 'a' represents the ratio of the desired signal component at said second intensity to the desired signal component at said first intensity, 'b' represents the ratio of the second harmonic at said first intensity to the desired signal component at said first intensity, and 'c' represents the ratio of the second harmonic at said second intensity to the desired signal component at said second intensity.

31. The method of claim 21, wherein said reflector repeatedly moves through a range of motion to modulate said optical measurement signal, and step (b) further includes:
 (b.1) sampling said modulated signal for a portion of each reflector movement iteration.

32. The method of claim 31, wherein step (b.1) further includes:
 (b.1.1) sampling said modulated signal for less than half of each reflector movement iteration.

33. A method for measuring linearity of an optical detector comprising:
 (a) generating at least two modulated optical measurement signals with different intensities for detection by said optical detector; and
 (b) sampling and processing said modulated measurement signals detected by said optical detector, wherein said sampled signals each include a desired component, a reflection component associated with reflections of said optical measurement signal and a non-linearity component associated with optical detector non-linearity, said reflection and non-linearity components residing within a second harmonic of each sampled optical measurement signal with said reflection component varying in a first proportion to an intensity of said measurement signal and said non-linearity component varying in a second different proportion to said measurement signal intensity; and (c) determining said non-linearity component within said second harmonic of said sampled optical measurement signals based on said component variations with different measurement signal intensities to produce said optical detector non-linearity.

34. The method of claim 33, wherein step (a) further includes:
(a.1) modulating each optical measurement signal in accordance with a position of a movable reflector; and
step (b) further includes:
(b.1) sampling each modulated signal in accordance with said reflector position.

35. The method of claim 34, wherein said reflector repeatedly moves through a range of motion to modulate each optical measurement signal, and step (b.1) further includes:
(b.1.1) sampling each modulated signal for a portion of each reflector movement iteration.

36. The method of claim 33, wherein step (a) further includes:
(a.1) varying optical measurement signal intensity without affecting said reflection component of each sampled signal.

37. The method of claim 33, wherein step (a) further includes:

(a.1) generating at least one optical signal from a target object representing ambient energy for detection by said optical detector; and
step (c) further includes:
(c.1) combining each measurement signal with at least one optical signal from said target object to remove said ambient energy and perform said harmonic analysis for said combined signal to determine said optical detector non-linearity.

38. The method of claim 33, wherein step (a) further includes:
(a.1) generating said measurement signals at first and second different intensities; and
step (c) further includes:
(c.1) determining said optical detector non-linearity in accordance with the following expression:

$$\text{Non} - \text{Linearity Magnitude} = \left[\frac{b-c}{1-a}\right];$$

wherein 'a' represents the ratio of the desired signal component at said second intensity to the desired signal component at said first intensity, 'b' represents the ratio of the second harmonic at said first intensity to the desired signal component at said first intensity, and 'c' represents the ratio of the second harmonic at said second intensity to the desired signal component at said second intensity.

* * * * *